United States Patent [19]

Scannell et al.

[11] 4,115,105

[45] Sep. 19, 1978

[54] L-2-AMINO-4-(2-AMINOETHOXY)-BUTANOIC ACID

[75] Inventors: James Parnell Scannell, North Caldwell; Arthur Stempel, Teaneck, both of N.J.

[73] Assignee: Hoffmann-La Roche Inc., Nutley, N.J.

[21] Appl. No.: 828,389

[22] Filed: Aug. 29, 1977

Related U.S. Application Data

[63] Continuation of Ser. No. 629,425, Nov. 6, 1975, abandoned, which is a continuation of Ser. No. 430,373, Jan. 2, 1974, abandoned.

[51] Int. Cl.$^2$ .................... A01N 9/24; C07C 101/24
[52] U.S. Cl. ..................................... 71/113; 562/564; 71/88; 560/12; 560/13; 560/158; 560/169; 426/268; 560/150; 560/159
[58] Field of Search ..................... 71/113; 260/534 M

[56] References Cited

U.S. PATENT DOCUMENTS

| | | | |
|---|---|---|---|
| 2,959,614 | 11/1960 | McCord et al. | 260/534 M |
| 3,751,459 | 8/1973 | Berger et al. | 260/534 M |
| 3,865,694 | 2/1975 | Berger et al. | 195/80 R |
| 3,869,277 | 3/1975 | Berger et al. | 71/113 |
| 3,887,615 | 6/1975 | Keith et al. | 260/534 M |

*Primary Examiner*—James O. Thomas, Jr.
*Assistant Examiner*—G. T. Breitenstein
*Attorney, Agent, or Firm*—Samuel L. Welt; George M. Gould; Frank P. Hoffman

[57] ABSTRACT

L-2-amino-4-(2-aminoethoxy)-butanoic acid, methods for its preparation and novel intermediates employed in these processes are disclosed. L-2-amino-4-(2-aminoethoxy)-butanoic acid enhances ethylene production in fruit and therefore has utility as a ripening agent and as an abscission agent.

5 Claims, No Drawings

L-2-AMINO-4-(2-AMINOETHOXY)-BUTANOIC ACID

This is a continuation, of application Ser. No. 629,425 filed Nov. 6, 1975 now abandoned which in turn is a continuation of Ser. No. 430,373 filed Jan. 2, 1974, now abandoned.

DETAILED DESCRIPTION OF THE INVENTION

The present invention is directed to a novel substituted butanoic acid and to methods of preparing this material. More particularly, the present invention relates to the new substance L-2-amino-4-(2-aminoethoxy)-butanoic acid, i.e. the L-antipode of a compound of the formula

and the pharmaceutically acceptable acid addition salts thereof.

The compounds of formula I above can be prepared following several synthetic approaches. In one such process aspect, the compound of formula I above can be prepared by the catalytic reduction of the known compound L-trans-2-amino-4-(2-aminoethoxy)-3-butenoic acid, i.e. the L-antipode of the compound of the formula

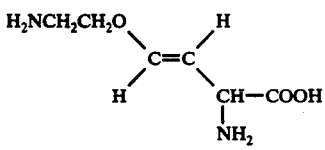

The compound of formula II above is known; its preparation is described in U.S. Pat. No. 3,751,459 issued Aug. 7, 1973 in the names of Berger, Pruess and Scannell.

Conversion of the compound of formula II above to the desired product of formula I is accomplished by catalytic reduction. Suitable reducing systems for this purpose include hydrogen in the presence of 5% palladium on charcoal or hydrogen in the presence of 10% platinum on charcoal. This catalytic reduction is expediently effected in the presence of an invert solvent such as water, lower alkanols such as methanol, ethanol and the like or mixtures of water and a lower alkanol. Temperature and pressure are not critical to this process aspect and thus the reaction may be performed at room temperature or above, with room temperature and atmospheric pressure being the preferred conditions.

Alternatively, the desired compound of formula I above may be prepared by the resolution of the corresponding racemic compound, D,L-2-amino-4-(2-aminoethoxy)butanoic acid. This racemic compound is novel and as such forms a part of the present invention. It can be prepared by condensing a compound of the formula

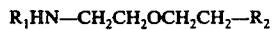

wherein $R_1$ signifies a suitable nitrogen protecting group and $R_2$ signifies chlorine, bromine or iodine
with the alkali metal derivative of a compound of the formula

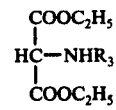

wherein $R_3$ signifies a suitable nitrogen protecting group.

The alkali metal derivative of the compound of formula IV above may be prepared following conventional techniques, such as by treating said compound with an alkali metal alkoxide, for example sodium methoxide, or an alkali metal hydride such as sodium hydride. The condensation of the compounds of formulae III and IV yields a compound of the formula

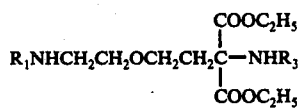

wherein $R_1$ and $R_3$ are as described above and can be the same or different protecting groups.

Suitable nitrogen protecting groups for the purposes of the above discussed condensation reaction include acyl groups such as acetyl, sulfonyl groups such as tosyl or mesyl, the carbobenzoxy group or the phthalimido group. It is understood that if $R_1$ or $R_3$ signifies a phthalimido group, the nitrogen atom does not carry a hydrogen atom.

The condensation of the compounds of formulae III and IV can be conducted without a solvent system or in the presence of an inert organic solvent. Suitable solvents for this purpose include alcohols such as methanol, ethanol and the like, ethers such as tetrahydrofuran, and dimethylformamide (DMF), with DMF being the preferred solvent. If $R_2$ signifies chlorine, it may be expedient to add potassium iodide to the reaction mixture so that the more reactive iodide ion replaces the chloride ion. This reaction is effected at elevated temperatures with a temperature in the range of from about 120° to about 160° C. being preferred.

The protecting groups present in the resulting compound of formula V are then removed to yield D,L-2-amino-4-(2-aminoethoxy)-butanoic acid. Removal of the protecting groups is accomplished following conventional techniques. For example, the compound of formula V wherein the protecting groups are phthalimido groups can be treated with an aqueous mineral acid, such as hydrochloric acid, to effect acid hydrolysis of the phthalimido groups. If the protecting groups present in the formula V compound are carbobenzoxy groups, the N-protective group can be removed either by hydrogenolysis or by treatment with hydrogen bromide in acetic acid. If the N-protective group is a tosyl group, it can be removed, for example, by reductive cleavage with sodium in liquid ammonia.

Resolution of the racemic compound obtained as described above is then accomplished by first preparing the racemic diacylated product. Thus D,L-2-amino-4-(2-aminoethoxy)-butanoic acid is treated with a conventional acylating agent, such as acetic anhydride, acetyl chloride, chloroacetyl chloride, and the like. The diacylated product thus obtained is then incubated with a suitable acylase, such as hog renal acylase, which resolves the racemic compound into a mixture of D and L compounds. The compound of formula I above and the corresponding D-antipode can then be obtained by separating the D and L materials resulting from the acylase incubation, and removing the acyl groups by acid hydrolysis using for example aqueous hydrochloric acid. In the final crystallization of the compound of formula I, this compound can be obtained as a zwitterion or as its mono- or di-acid salt, for example as its mono- or di-hydrochloride.

The novel compound of formula I above forms pharmaceutically acceptable acid addition salts with organic or inorganic acids. Suitable acids for this purpose include the hydrohalic acids such as hydrochloric acid and hydrobromic acid, other mineral acids such as sulfuric acid, phosphoric acid, nitric acid and the like, and organic acids such as tartaric acid, citric acid, acetic acid, formic acid, maleic acid, succinic acid and the like.

The compound of formula I above either alone or in combination with ascorbic acid enhances ethylene production in fruits and therefore is useful as an abscission agent.

The role of ethylene in the ripening of fruits has been recognized in the art for over 30 years. It is known that the production of ethylene in maturing fruits increases while the fruit separates from its pedicel. This knowledge can be utilized to demonstrate the efficacy of an abscission compound in regard to its influence on fruit to accelerate or increase the production of ethylene. Since oranges can be considered a typical fruit representative of those amenable to treatment by chemical abscission agents, the efficacy of the compound of formula I as an abscission agent may be illustrated with respect thereto.

The ability of the compound of formula I above to enhance ethylene production is demonstrated in the following test procedure. Whole fresh green oranges and semi-ripe yellow oranges were sprayed with a 0.1% solution of the compound of formula I. The control oranges were treated with distilled water. All sprays contained 0.1% Aerosol OT (sodium dioctyl sulfosuccinate, SDS) as the wetting agent. SDS in the solutions assured a thin film like coverage on the waxy skin of the oranges thereby producing an increased surface area for the absorption of the active material. The treated fruits were then placed in polyethylene bags, glass jars or aluminum cans and sealed. Air space of the bags or cans was sampled periodically for ethylene with gas tight syringes.

Ethylene production in the reaction vessels was determined by gas chromatography. A Hewlett Packard, Series 5750B, Dual Flame Detector Research Gas Chromatograph was fitted with 10 foot $\times$ ⅛ inch stainless steel column packed with alumina (5% $H_2O$ on neutral alumina) to determine ethylene. The instrument was operated at 45° C. The carrier gas was helium with a flow rate of 25 ml per minute.

The ethylene nature of the gas measured was established by retention time in relation to pure ethylene and it was confirmed by mercuric perchlorate [$Hg(ClO_4)_2$] reaction and mass spectrometry. Mercuric perchlorate absorbs ethylene while hydrochloric acid (HCl) releases the absorbed gas. The disappearance and the reappearance of the ethylene component of the gas was noted in samples treated first with 1-2 ml 0.2M $Hg(ClO_4)_2$ and then with 1 ml 2N HCl.

The mass spectrum of pure ethylene gas was found to be comparable to the component measured as such and the ethylene nature of the gas produced in the reaction vessels was established.

The results for this test procedure for the green oranges are reported in Table 1. These results show that in the control sample a slight amount of ethylene was produced while the rate of ethylene production was greatly enhanced in the oranges treated with the compound of formula I. The amount of ethylene produced is expressed in microliters of ethylene/ml.

TABLE I

Ethylene production by green oranges sprayed 1-1.3 gms/orange incubated in polyethylene bags at room temperature for 14 days

| SAMPLE | μl E/ml |
|---|---|
| Orange + Distilled water | 0.0008 |
| Orange + 0.1% L-2-amino-4-(2-aminoethoxy)-butonic acid | 0.0050 |

The results for this test procedure for the semi-ripe yellow oranges are reported in Table 2. These results shown in Table 2 are similar to those in Table 1 in that again the compound of formula I greatly enhanced the rate of ethylene production in the oranges.

TABLE 2

Ethylene production by yellow oranges sprayed 1-1.3 gms/orange incubated in metal cans at room-temperature

| SAMPLE | μl E/ml | |
|---|---|---|
| | 10 days | 18 days |
| Orange + Distilled water | 0.0009 | 0.0007 |
| Orange + 0.1% L-2-amino-4-(2-aminoethoxy)-butanoic acid | 0.0015 | 0.0044 |

As indicated by the above test procedures, the compound of formula I above is useful as a ripening agent or as an an abscission agent in fruit. The results discussed above show that the compound of formula I when administered as the sole abscission agent enhances ethylene production. In addition, it has been found that a synergistic effect is obtained from combinations of the compound of formula I and ascorbic acid for abscission of fruit. This synergistic effect is demonstrated by repeating the same test procedures described above using green oranges, spraying the oranges with:

Treatment 1-distilled water

Treatment 2–0.1% L-2-amino-4-(2-aminoethoxy)-butanoic acid

Treatment 3-Formulation A (ascorbic acid-58.9%, Disodium phosphate-4.1%, monosodium phosphate-33.9%, copper sulfate-0.1% and aerosol OT-3.0%-percentages in weight by weight) at 4% ascorbic acid Treatment 4-Formulation A at 4% ascorbic acid and 0.1% L-2-amino-4-(2-aminoethoxy)-butanoic acid The result for this test procedure is set forth in Table 3 below. From these results, it can be seen that a synergistic effect is obtained from the combination of the compound of formula I and ascorbic acid for abscission of fruit.

TABLE 3

Ethylene production by green oranges sprayed 1-1.3 gms/orange incubated in polyethylene bags at room-temperature for 14 days

| SAMPLE | μl E/ml |
|---|---|
| Treatment 1 | 0.0008 |
| Treatment 2 | 0.0050 |
| Treatment 3 | 0.0032 |
| Treatment 4 | 0.0225 |

The synergistic effect between the compound of formula I above and ascorbic acid for abscission of citrus is also demonstrated in the following field trials. These trials were conducted at Vero Beach, Florida and the applications of the test materials were made in early May. Selected branches of Valencia orange trees were sprayed, each treatment was replicated twice using branches on different trees. Treatments were applied to run-off using a one quart carbon dioxide sprayer equipped with a single 8002 Tee Jet nozzle and a pressure of 34 psi. The non-tonic surfactant X-77 spreader (Colloidol Products Corp., Saulsalito, California) was added to all spray solutions at 0.5%. The composition of the sprays applied to the branches were as follows:

Treatment 1–0.4%-L-2-amino-4-(2-aminoethoxy)-butanoic acid

Treatment 2–1.0% ascorbic acid

Treatment 3–0.1% L-2-amino-4-(2-aminoethoxy)-butanoic acid + 0.1% ascorbic acid

Treatment 4–0.2% L-2-amino-4-(2-aminoethoxy)-butanoic acid + 0.2% ascorbic acid

The only rainfall that occurred during the 14 day treatment period fell on the ninth day and amounted to 0.77 inches. The maximum and minimum temperatures for the test period were as follows:

| Day | Maximum(° F) | Minimum(° F) |
|---|---|---|
| 1 | 78 | 73 |
| 2 | 79 | 75 |
| 3 | 80 | 72 |
| 4 | 80 | 73 |
| 5 | 79 | 73 |
| 6 | 77 | 60 |
| 7 | 80 | 72 |
| 8 | 83 | 76 |
| 9 | 86 | 76 |
| 10 | 85 | 76 |
| 11 | 86 | 73 |
| 12 | 90 | 75 |
| 13 | 88 | 78 |
| 14 | 90 | 76 |

The number of fruit was counted on each branch at time of treatment and at 7 and 14 days after treatment. The data on the amount of fruit abscission 7 and 14 days after treatment are presented in Table 4.

TABLE 4

| Average percent[a] Fruit abcission of Valencia oranges | | |
|---|---|---|
| SAMPLE | 7 days | 14 days |
| Untreated | 0 | 0 |
| Treatment 1 | 0 | 0 |
| Treatment 2 | 11 | 22 |
| Treatment 3 | 0 | 25 |
| Treatment 4 | 43 | 57 |

[a]average of two replications

Compositions containing the compound of formula I and ascorbic acid can be applied to the fruit-bearing trees in liquid or powder formulations. Application may be made to the roots, trunks, limbs, leaves or fruit. For example, the abscission compositions can be dusted on the trees from airplanes or applied to the base of the trees in order to be absorbed by the roots. The preferred method of application and the most efficient is to apply the compositions to the trees from above in the form of an aqueous spray. If desired, an oily spray may be used.

In order to achieve the most efficient use of the abscission compositions, it is preferred to apply them from about 2 to 7 days prior to harvesting of the mature fruit. It is preferred to incorporate a conventional adhesive agent into the abscission compositions of the invention as a precaution against a rainfall occurring after application and washing the abscission composition from the fruit. Examples of such adhesive agents include glue, casein, salts of alginic acids, cellulose gums and their derivatives, polyvinyl pyrrolidone, vegetable gums, propylene glycol, invert syrup, corn syrup and the like.

These abscission compositions can contain, in addition to the compound of formula I and ascorbic acid, a water-soluble cupric salt such as cupric sulfate, cupric chloride and the like, a buffer and a surfactant. If desired, inert materials conventionally used in agriculture for applications to trees may be utilized.

In order to form the liquid spray formulations for the abscission compositions the active ingredients are dispersed in a carrier such as, for example, water or other suitable liquids. In liquid spray compositions, it is preferred to include from about 0.1% to about 0.5% by weight, based on the weight of the carrier, of a surface active agent. The surface active agents may be anionic, cationic or non-ionic in character. Typical classes of surface active agents include alkylsulfonates, alklarylsulfonates, alkylsulfates, alkylamide sulfonates, alkylaryl polyether alcohols, fatty acid esters of polyhydric alcohols, ethylene oxide addition products of such esters; addition products of long chain mercaptans and ethylene oxide; sodium alkyl benzene sulfonates having from 14 to 18 carbon atoms, alkylphenylethylene oxides, e.g. para-nonylphenol condensed with 10 ethylene oxide units or paraisooctyl phenol condensed with 10 ethylene oxide units or with two ethylene oxide units or with 16 ethylene oxide units, and soaps, e.g. sodium stearate and sodium maleate. Typical surface active agents are: sodium salt of propylated naphthalenesulfonic acids; Aerosol OT manufactured by American Cyanamide Co. New York, New York: X-77 Spreader manufactured by Colloidal Products Corp., Saulsalito, California; the sodium salt of modified alcohol sulfate from coconut fatty acids; the sodium salt of sulfonated monoglyceride of coconut fatty acids; the sodium sulfonate of butylbisphenyl sorbitan sesquiolate; lauryltrimethyl ammonium chloride; octadecyltrimethyl ammonium chloride; polyethyleneglycol laurylether; Daxad No. 11 manufactured by Dewey and Almy Chemical Co., Cambridge, Mass. (sodium salt of polymerized alkyl aryl sulfonic acid); sodium oleate sulfate; sodium lauryl sulfate; Ethofats manufactured by Armour & Co. Chicago, Ill. (polyethylene esters of fatty acids or rosin acids); Ethomeens manufactured by Armour & Co., Chicago, Ill. (polyethylene glycol derivatives of long chain alkylamines), Tritons manufactured by Rohm & Haas Co., Philadelphia, Pa. (alkylaryl polyether alcohols, sulfonates, and sulfates of the non-ionic, cationic and anionic types) and the like.

These abscission compositions can be used to abscind a variety of fruits from trees. Typical fruits with which these compositions are efficacious include oranges, olives, apples, cherries and the like. The compositions of the invention are most efficacious in the abscission of citrus fruits, e.g., oranges, grapefruit and the like.

If, under particular application conditions, it is desirable to adjust the pH of the abscission compositions, this can be done following conventional techniques. For example, buffers such as disodium phosphate, monosodium phosphate, sodium dibasic phosphate monohydrate and the like or mixtures of these can be incorporated into the abscission compositions to adjust the pH to the desired range.

The nature and objects of the present invention can be more fully understood by making reference to the following examples. Unless otherwise indicated, all temperatures are given in degrees Centigrade.

EXAMPLE 1

Preparation of L-2-amino-4-(2-aminoethoxy)butanoic acid hydrochloride

A solution of 125 mg of L-trans-2-amino-4-(2-aminoethoxy)-3-butenoic acid in 50 ml 90% methanol-water was reduced with $H_2$ at 1 atmosphere and 25° in the presence of 150 mg 5% Pd on charcoal. The catalyst was removed by filtration, the filtrate partially evaporated under reduced pressure and the concentrate applied to 5 ml Biorad AG50X4 (100–200 mesh) cation exchange resin in the $H^+$ form. The resin was then eluted successively with 10% pyridine solution and 1M $NH_4OH$ solution. The eluates were evaporated to dryness under reduced pressure.

Thin layer chromatography of the pyridine eluate indicated that the major ninhydrin positive component was 2-aminobutanoic acid. The ammonia eluate residue was taken up in a small volume of $H_2O$, the pH was adjusted to 3.8 with 1N HCl the residue concentrated to dryness and the above-identified product was crystallized from 2 ml methanol, m.p. 205°–207°.

EXAMPLE 2

Preparation of L-2-amino-4-(2-aminoethoxy)-butanoic acid hydrochloride

A solution of 125 mg. of L-trans-2-amino-4-(2-aminoethoxy)-3-butenoic acid in 50 ml 90% methanol-water was reduced with $H_2$ at 1 atmosphere and 25° in the presence of 75 mg 10% platinum on charcoal. The catalyst was removed by filtration, the filtrate partially evaporated under reduced pressure and the concentrate applied to 5 ml. Biorad AG50X4 (100–200 mesh) cation exchange resin in the $H^+$ form. The resin was then eluted successively with 10% pyridine solution and 1M $NH_4OH$ solution. The eluates were evaporated to dryness under reduced pressure. Thin layer chromatography of the pyridine eluate indicated that the major ninhydrin positive component was 2-aminobutanoic acid. The ammonia eluate residue were taken up in a small volume of water, the pH was adjusted to 3.8 with 1N HCl, the residue concentrated to dryness and the above-identified product was crystallized from 2 ml of methanol, m.p. 205°–207°.

EXAMPLE 3

Preparation of L-2-amino-4-(2-aminoethoxy)butanoic acid hydrochloride

A solution of 7.85 g of L-trans-2-amino-4-(2-aminoethoxy)-3-butenoic acid (40 mmoles) in 200 ml $H_2O$ was treated in a Parr apparatus at 1 atmosphere pressure and 25° for 2 hours with hydrogen in the presence of 1 g 5% Pd on charcoal. The solution was then filtered and the product was adsorbed on 70 ml AG50WX-4 cation exchange resin (100–200 mesh in the $H^+$ form). The resin was eluted with 10% aqueous pyridine solution and the eluate was evaporated under reduced pressure to a 24 mg residue. The resin was then eluted with 1M $NH_4OH$, the eluate partially evaporated under reduced pressure, the concentrate adjusted to pH 5.0 with 18 ml 2N HCl and the remaining solvent evaporated under reduced pressure. The residue was taken up in hot methanol and the above-identified product crystallized after addition of ethanol m.p. 208°–211°.

EXAMPLE 4

Preparation of D,L-2-amino-4-(2-aminoethoxy)butanoic acid hydrochloride

2-Chloroethyl-2'-Chloroethyl-2'-phthalimidoethyl ether, (37.5 mmole, 9.4 g), sodium diethyl phthalimidomalonate, (25 mmole, 8.2 g) and potassium iodide (2.5 mmoles, 0.4 g) were dissolved in 10 ml dimethylformamide and the solution was maintained at 153° for 4 hrs by which time titration of a small portion indicated that 99% of the malonate reagent had reacted. The product, diethyl 2-phthalimido-2-(phthalimidoethoxyethyl)-malonate could be crystallized from ethanol, m.p. 96°–98°. However it was more efficient to proceed by precipitating the crude condensation product by addition of 4 volumes of water and triturating the precipitate 2 times with 40 ml water.

The crude condensation product from 4/5 of the original reaction mixture was dissolved in 20 ml ethanol, 40 ml of an aqueous solution of 5 N NaOH was added and the solution was refluxed for 1 hour. The ethanol was then allowed to boil off and the cooled solution was adjusted to pH 1 with 6 N HCl. The aqueous phase was decanted from the oil which formed, and the oil was refluxed in 120 ml 6 N HCl for 90 minutes. After cooling and filtering, the solvent was removed by evaporation under reduced pressure and the residue was dissolved in water and applied to 100 ml Bio-Rad AG50X4 (50–100 mesh) cation exchange resin in the $H^+$ form. The resin was eluted first with 100 ml 20% aqueous pyridine solution and then with 200 ml aqueous 1 N $NH_4OH$. The latter eluate was partially evaporated under reduced pressure and the pH was then adjusted to 3.5 with 22 meq HCl. The water was removed by evaporation under reduced pressure, the residue dissolved in a small amount of methanol, and after addition of ethanol to a total volume of 50 ml, the above-identified product crystallized during storage at 0°, m.p. 175°–177°.

EXAMPLE 5

Resolution of D,L-2-amino-4-(2-aminoethoxy)butanoic acid

A solution of D,L-2-amino-4-(2-aminoethoxy)-butanoic acid, 1g (5 mmole) in 5 ml 2 N NaOH, was treated with 1.25 ml, 11 mmoles, chloroacetylchloride and the pH was maintained at 10.2 by the addition of 2 N NaOH while the temperature was kept at 5°. After 45 min the pH was adjusted to 1.0 with 2 N HCl. The product did not precipitate but was extracted with 5 × 10 ml ethyl ether. The combined extracts were back extracted with 10 ml $H_2O$ and the organic phase evaporated at reduced pressure to 1.6 g syrup. The syrup was taken up in ethanol and a saturated solution of LiOH was added to an apparent pH of 7. The solvent was evaporated under reduced pressure to yield the lithium salt of D,L-2-chloroacetylamino-4-(2-chloroacetylaminoethoxy) butanoic acid, which was crystallized from 5 ml 50% ether-ethanol, m.p. 201°–203°.

A solution of 642 mg of the so-obtained di-acylated product in 20 ml deionized water was treated with 30 mg hog renal acylase at 37° and pH 7.2 for 21 hours. The solution was then applied to a column containing 10 ml Biorad AG50WX4 cation exchange resin (50–100 mesh in the $H^+$ form). The column effluent plus a 50 ml water wash was concentrated to 20 ml, the pH readjusted to 7.2 with LiOH solution, an additional 30 mg acylase added and another incubation carried out for 18 hours. The solution was then reapplied to the same column and the column effluent and water wash were again put through the same procedure. From the final column effluent and wash, the lithium salt was made and D-2-chloroacetylamino-4-(2-chloroacetylaminoethoxy)butanoic acid crystallized from ethanol after removing the acylase by filtration from an aqueous ethanol suspension. After recrystallization the product showed a m.p. of 210°.

The above described resin was then eluted with 100 ml 10% aqueous pyridine solution. The eluate was concentrated under reduced pressure and L-2-amino-4-(2-chloroacetylaminoethoxy) butanoic acid was crystallized from ethanol water, m.p. after recrystallization 139°-141°.

The chloroacetyl groups were removed from both D-2-chloroacetylamino-4-(2-chloroacetylaminoethoxy)butanoic acid and L-2-amino-4-(2-chloroacetylamino-ethoxy)butanoic acid by refluxing 0.8 mmole of each for 2 hours in 10 ml 2N HCl. After evaporation at reduced pressure each preparation was taken up in water and applied to a 5 ml column of Biorad AG50WX4 (50-100 mesh) cation exchange resin in the H+ form. After washing the columns with aqueous pyridine solution, the products were eluted with 50 ml 1 N NH$_4$OH. The solvent was partially evaporated under reduced pressure, the pH adjusted to 4.5 with 1 N HCl and the products crystallized from ethanol-water. Thus, from D-2-chloroacetylamino-4-(2-chloroacetylaminoethoxy)butanoic acid there was obtained D-2-amino-4-(2-aminoethoxy)butanoic acid hydrochloride, m.p. 206° and from L-2-amino-4-(2-chloroacetylaminoethoxy)-butanoic acid there was obtained L-2-amino-4-(2-aminoethoxy)butanoic acid hydrochloride, m.p. 204°-206°.

We claim:

1. The L-antipode of the compound of the formula

and the pharmaceutically acceptable acid addition salts thereof.

2. The compound of claim 1 which is L-2-amino-4-(2-aminoethoxy)-butanoic acid.

3. D,L-2-amino-4-(2-aminoethoxy)-butanoic acid.

4. A method of increasing the ripening of fruit which comprises the application to said fruit of an effective ethylene enhancing amount of an abscission agent selected from the group consisting of the L-antipode of the compound of the formula

and the pharmaceutically acceptable acid addition salts thereof.

5. The abscission agent of claim 4 which is L-2-amino-4-(2-aminoethoxy)-butanoic acid.

* * * * *